United States Patent [19]

Bartfai

[11] Patent Number: 5,225,193
[45] Date of Patent: Jul. 6, 1993

[54] BORDETELLA TOXIN PEPTIDES AND VACCINES

[75] Inventor: Tamas Bartfai, Stocksund, Sweden

[73] Assignee: Trion-Forskining-Och Utvecklings Aktiebolag, Sollentuna, Sweden

[21] Appl. No.: 346,837

[22] PCT Filed: Oct. 19, 1987

[86] PCT No.: PCT/SE87/00476
§ 371 Date: May 24, 1989
§ 102(e) Date: May 24, 1989

[87] PCT Pub. No.: WO88/02754
PCT Pub. Date: Apr. 21, 1988

[30] Foreign Application Priority Data

Oct. 20, 1986 [SE] Sweden ............................. 8604445

[51] Int. Cl.$^5$ .............................................. A61K 39/10
[52] U.S. Cl. .......................................... 424/88; 424/92; 530/325; 530/326; 530/825; 930/200
[58] Field of Search ............... 424/88, 92, 9; 530/325, 530/326, 825; 514/13

[56] References Cited

U.S. PATENT DOCUMENTS 4,762,710  8/1988  Sekura .................................... 424/92
5,000,952  3/1991  Steinman et al. ...................... 424/92

OTHER PUBLICATIONS

Askelof et al. *Proc. Natl. Acad. Sci. U.S.A.*, 87, 1347–1351, Feb. 1990.
Olin et al., *JAMA*, Jan. 27, 1989, vol. 261, No. 4, p. 560.
Alberts et al. in Molecular Biology of the Cell pp. 177–178, 1983.

*Primary Examiner*—Robert J. Hill, Jr.
*Assistant Examiner*—Nina Ossanna
*Attorney, Agent, or Firm*—Bacon & Thomas

[57] ABSTRACT

The following new polypeptides are described: (a) H-$X^1$-Asp-Asp-Pro-Pro-Ala-Thr-Val-Tyr-Arg-Tyr-Asp-Ser-Arg-Pro-Pro-Glu-Asp-$X^2$-Y, (b) H-$X^1$-Ser-Glu-Tyr-Leu-Ala-His-Arg-Arg-Ile-Pro-Pro-Glu-Asn-Ile-Arg-Arg-Val-Thr-Arg-Val-$X^2$-Y, (c) H-$X^1$-Ala-Phe-Val-Ser-Thr-Ser-Ser-Ser-Arg-Arg-Tyr-Thr-Glu-Val-Tyr-$X^2$-Y, (d) H-$X^1$-Gly-Ile-Thr-Gly-Glu-Thr-Thr-Thr-Thr-Glu-Tyr-Ser-Asn-Ala-Arg-Tyr-Val-$X^2$-Y, and (e) H-$X^1$-Leu-Glu-His-Arg-Met-Gln-Glu-Ala-Val-Glu-Ala-Glu-Arg-Ala-Gly-Arg-Gly-Thr-Gly-His-Phe-Ile-$X^2$-Y, in which $X^1$ and $X^2$ each represents an optional coupling-facilitating amino acid residue, and Y represents —OH or —$NH_2$. Additionally, there is described an artificial pertussis toxin antigen, which mainly consists of at least one peptide sequence reacting with antibodies induced by the native pertussis toxin selected from the above polypeptides (a) to (e) and parts thereof. The above described artificial pertussis toxin antigen is included as a diagnostic antigen in a diagnostic immunoassay kit for the determination of antibodies induced by the native pertussis toxin in a sample of biological fluid, and as an immunizing component in a vaccine composition against whooping cough, respectively. Furthermore there is described an intradermal skin test composition comprising the above described artificial pertussis toxin antigen.

6 Claims, No Drawings

BORDETELLA TOXIN PEPTIDES AND VACCINES

The present invention relates to new polypeptides, to artificial pertussis toxin antigens, which mainly consist of peptide sequences reacting with antibodies induced by the native pertussis toxin selected from the new polypeptides and parts thereof, to a diagnostic immunoassay kit comprising as a diagnostic antigen, said antigens reacting with antibodies induced by the native pertussis toxin, to a vaccine composition comprising as an immunizing component antigens selected from said antigens reacting with antibodies induced by the native pertussis toxin, and to an intradermal skin test composition comprising antigens selected from said antigens reacting with antibodies induced by the native pertussis toxin.

BACKGROUND

Up to now no peptide antigens constituting part of pertussis toxin have been identified in the art. Since such antigens have not been provided, it has not been possible to develop diagnostic immunoassay kits comprising such antigens as diagnostic antigens nor to develop vaccines against whooping cough based on such antigens.

Diagnosis of whooping cough with the aid of antigens directed against *Bordetella pertussis* antibodies or proteins produced by *B. pertussis* have been published, but as diagnostic antigen there has been used fimbrial hemagglutinin (see e.g. Granström, M., Granstroöm, G., Lindfors, A., and Askelöf, P. 1982. Serologic diagnosis of whooping cough by an enzyme-linked immunosorbent assay using fimbrial hemagglutinin as antigen. J. Infect. Dis. vol 146:741-745), or sonicated *B. pertussis* bacteria (see e.g. Goodman, Y. E., Wort, A. J. and Jackson, F. L. 1981. Enzyme-linked immunosorbent assay for detection of pertussis immunoglobulin A in nasopharyngeal secretions as an indicator of recent infection. J. Clin. Microbiol. vol. 13:286-292, and Viljanen, M. K., Ruuskanen, O., Granberg, C. and Salmi, T. T. 1982. Serological diagnosis of pertussis: IgM, IgA and IgG antibodies against *Bordetella pertussis* measured by enzyme-linked immunosorbent assay. Scand. J. Infect. Dis. vol. 14:112-117).

As is well known in the art currently used vaccines against whooping cough are in USA and many other countries based on inactivated *Bordetella pertussis* bacteria. M. Pittman proposed 1979 that whooping cough was mediated by an exotoxin (pertussis toxin) (see Pittman, M. 1979. Pertussis toxin: The cause of the harmful effects and prolonged immunity of whooping cough. A hypothesis. Rev. Infect. Dis. vol. 1:401-412) and in Japan acellular vaccines comprising inactivated pertussis toxin are currently in use.

Recently the nucleotide sequence of pertussis toxin was published (Locht, C. and Keith, J. M., 1986. Pertussis Toxin Gene: Nucleotide Sequence and Genetic Organization, Science, vol. 232, p. 1258-1264). In this article the authors suggest i.a. that synthetic oligopeptides that include protective epitopes also will be useful in the development of a new generation of vaccines, but there is no teaching or suggestion of such epitopes.

Another recently published article concerning pertussis toxin genes is: Nicosia, A., Perugini, M., Franzini, C., Casagli, M. C., Borri, M. G., Antoni, G., Almoni, M., Neri, P., Ratti, G., and Rappuoli, R., 1986. Cloning and sequencing of the pertussis toxin genes: Operon structure and gene duplication. Proc. Natl. Acad. Sci. USA, vol. 83, 4631-4635. In this publication it is stated i.a. that "Manipulation of the toxin gene by genetic engineering could be a way to produce large amounts of detoxified protein". This is merely a suggestion and no manipulated toxin gene is disclosed.

Yet another publication in this field is: Engström, O., Rodmalm, K., Jörnvall, H., Lundquist, G., Kálmán, M., Simonscits, A., Bartfai, T., Löfdahl, S., and Askelöf, P., 1986. Characterization of the N-terminal structure of pertussis toxin subunit S1 and hybridization of oligodeoxyribonucleotide probes with *Bordetella pertussis* DNA fragment, FEMS Microbiology Letters, vol. 36, 219-223. Also this article makes suggestions, namely, "The gene may also be introduced into other organisms for production of toxin. Sequencing of the gene would allow synthesis of peptides corresponding to the antigenic epitopes of the toxin and hence to the development of a synthetic pertussis vaccine." However, the antigenic epitopes of the pertussis toxin have not been identified, synthesized nor tested.

As regards intradermal skin test compositions, such compositions for testing immunity against pertussis are hitherto not described in the art.

DESCRIPTION OF THE INVENTION

In one aspect of the invention there is provided five new polypeptides, namely a) the polypeptide $$H-X^1-Asp-Asp-Pro-Pro-Ala-Thr-Val-Tyr-Arg-Tyr-$$
$$Asp-Ser-Arg-Pro-Pro-Glu-Asp-X^2-Y$$

b) the polypeptide $$H-X^1-Ser-Glu-Tyr-Leu-Ala-His-Arg-Arg-Ile-Pro-$$
$$Pro-Glu-Asn-Ile-Arg-Arg-Val-Thr-Arg-Val-X^2-Y$$

c) the polypeptide $$H-X^1-Ala-Phe-Val-Ser-Thr-Ser-Ser-Ser-Arg-Arg-$$
$$Tyr-Thr-Glu-Val-Tyr-X^2-Y$$

d) the polypeptide $$H-X^1-Gly-Ile-Thr-Gly-Glu-Thr-Thr-Thr-Thr-Glu-$$
$$Tyr-Ser-Asn-Ala-Arg-Tyr-Val-X^2-Y, \text{ and}$$

e) the polypeptide $$H-X^1-Leu-Glu-His-Arg-Met-Gln-Glu-Ala-Val-Glu-$$
$$Ala-Glu-Arg-Ala-Gly-Arg-Gly-Thr-Gly-His-Phe-$$
$$Ile-X^2-Y$$

in which $X^1$ and $X^2$ each represents an optional coupling-facilitating amino acid residue, and Y represents —OH or —NH$_2$.

Examples of suitable optional amino acid residues are -Lys- and -Cys-. These optional amino acid residues facilitate the coupling of a carrier, such as bovine serum albumin, to said polypeptides.

These polypeptides have essential properties in common, i.a. their ability to react with antibodies from convalescent serum from whooping cough patients.

The polypeptides according to the invention have been synthesized in accordance with per se known solid phase techniques.

In another aspect of the invention there is provided an artificial pertussis toxin antigen, which mainly consists of at least one peptide sequence reacting with antibodies induced by the native pertussis toxin selected from the group consisting of a) the polypeptide $$H-X^1-Asp-Asp-Pro-Pro-Ala-Thr-Val-Tyr-Arg-Tyr-$$
$$Asp-Ser-Arg-Pro-Pro-Glu-Asp-X^2-Y$$

in which $X^1$ and $X^2$ each represents an optional coupling-facilitating amino acid residue, and Y represents —CH or —NH$_2$;
and parts thereof, b) the polypeptide $$H-X^1-Ser-Glu-Tyr-Leu-Ala-His-Arg-Arg-Ile-Pro-$$
$$Pro-Glu-Asn-Ile-Arg-Arg-Val-Thr-Arg-Val-X^2-Y$$

in which $X^1$ and $X^2$ each represents an optional coupling-facilitating amino acid residue, and Y represents —OH or —NH$_2$;
and parts thereof, c) the polypeptide $$H-X^1-Ala-Phe-Val-Ser-Thr-Ser-Ser-Ser-Arg-Arg-$$
$$Tyr-Thr-Glu-Val-Tyr-X^2-Y$$

in which $X^1$ and $X^2$ each represents an optional coupling-facilitating amino acid residue, and Y represents —OH or —NH$_2$;
and parts thereof, d) the polypeptide $$H-X^1-Gly-Ile-Thr-Gly-Glu-Thr-Thr-Thr-Thr-Glu-$$
$$Tyr-Ser-Asn-Ala-Arg-Tyr-Val-X^2-Y$$

in which $X^1$ and $X^2$ each represents an optional coupling-facilitating amino acid residue, and Y represents —OH or —NH$_2$;
and parts thereof, e) the polypeptide $$H-X^1-Leu-Glu-His-Arg-Met-Gln-Glu-Ala-Val-Glu-$$
$$Ala-Glu-Arg-Ala-Gly-Arg-Gly-Thr-Gly-His-Phe-$$
$$Ile-X^2-Y$$

in which $X^1$ and $X^2$ each represents an optional coupling-facilitating amino acid residue, and Y represents —OH or —NH$_2$;
and parts thereof.

The polypeptides according to the invention are able to react with antibodies induced by the native pertussis toxin and are able to induce antibodies, which react with the native toxin, in animals. Hence they can be considered as antigens. Being antigens, polypeptides according to the invention are likely to include shorter peptide sequences which on their own react with antibodies induced by the native pertussis toxin. The artificial pertussis toxin antigen reacting with antibodies induced by the native pertussis toxin according to the invention does not necessarily comprise more than one such shorter peptide sequence being part of one of the polypeptides of the invention together with a carrier, even though it preferably comprises several such shorter peptide sequences.

The expression "artificial pertussis toxin antigen", as it is used in this specification and appended claims, is contemplated to include pertussis toxin antigens that have been produced in an artificial manner, i.e. contrived through human effort and not by natural causes detached from human agency. Even though the peptide sequences constituting, or constituting part of, the artificial pertussis toxin antigen according to the invention have been chemically synthesized according to per se known solid-phase technique, said peptide sequences can be produced using some other techniques, e.g. synthesis in liquid phase by coupling one amino acid to the next in known manner, degradation, cloning etc, and it is intended that the expression "artificial" should cover products produced by any such technique.

The word "comprises" is used, in this specification and appended claims, to indicate that something is included, but that that something does not necessarily constitute the only thing included.

The expression "mainly consists of" in conjunction with "peptide sequences reacting with antibodies induced by the native pertussis toxin" is used to indicate that the ability of the artificial pertussis toxin antigen to react with antibodies induced by the native pertussis toxin derives from said peptide sequences".

The word "carrier" should be interpreted broadly, and the carrier can be anything to which the peptide in question can be linked by physical/chemical interaction, such as covalent binding, ionic binding, hydrogen binding or hydrophobic binding. Examples of such carriers are mineral carriers, e.g. aluminium hydroxide, calcium phosphate, etc., plastic surfaces, e.g. microplates, beads, etc., lipids, liposomes, carbohydrates, amino acids, peptides and proteins.

In still another aspect of the invention there is provided a diagnostic immunoassay kit for the determination of antibodies induced by the native pertussis toxin in a sample of biological fluid. The kit comprises as a diagnostic antigen at least one antigen selected from the artificial antigens reacting with antibodies induced by the native pertussis toxin according to the invention. Depending on the immunoassay used for the determination of antibodies induced by the native pertussis toxin the kit may comprise other suitable reagents, such as a carrier to which said diagnostic antigen is coupled, a positive standard serum sample, a negative standard serum sample, an enzyme conjugate, such as alkaline phosphatase or peroxidase, substrate for the enzyme conjugate, such as paranitrophenylphosphate, agar or agarose gel, radioactively labelled antigen, buffer solutions and/or washing solutions. Optionally all the reagents in the kit are contained in separate sealed test tubes or vials marked with specific labels.

The sample of biological fluid is preferably a nasopharyngeal secretion, saliva, blood or serum sample from an animal, e.g. a human.

Examples of immunoassays in which the kit according to the invention can be used are ELISA (enzyme-linked immunosorbent assay), Immunodiffusion, Radioimmunoassay (RIA), and Immunoelectrophoresis (IE).

When ELISA (enzyme-linked immunosorbent assay) is used the kit according to the invention will comprise
  a) a diagnostic antigen of the invention
  b) optionally a carrier for said diagnostic antigen
  c) optionally a positive standard serum sample
  d) optionally a negative standard serum sample
  e) an enzyme conjugate
  f) optionally a substrate for said enzyme conjugate
  g) optionally buffer solution(s), and
  h) optionally washing solution(s).

When immunodiffusion or immunoelectrophoresis (IE) is used the kit according to the invention will comprise the same as for ELISA, with the exception of items e) and f). Instead there is needed a gel, such as agar or agarose gel, but such a gel is normally not included in the kit, since it is commonly available.

When radioimmunoassay (RIA) is used the kit according to the invention will comprise the same as for ELISA, with the exception of items e) and f), which will be substituted for radioactively labelled antigen. Optionally there may also be included a solution for the precipitation of radioactively labelled antigen bound to antibodies, such as trichloroacetic acid or secondary antibodies.

In a further aspect of the invention there is provided a vaccine composition, which as an immunizing component comprises at least one antigen selected from the artificial pertussis toxin antigens reacting with antibodies induced by the native pertussis toxin, according to the invention, preferably in an amount effective to protect a subject from the disease whooping cough, and a nontoxic pharmaceutically acceptable carrier and/or diluent. The carrier is a carrier which has been defined herein above, and the diluent may be a conventional diluent used in the art, such as saline solution. The vaccine composition according to the invention may further comprise an antigen adjuvant in an amount which together with the amount of said antigen is effective to protect a subject from the disease whooping cough. Examples of commonly used adjuvants in vaccines for humans are so-called mineral carriers, e.g. phosphate or hydroxide of calcium or aluminium, to which the antigen in question is adsorbed. An example of commonly used veterinary vaccine adjuvant is Freund's Complete Adjuvant. The vaccine composition may additionally comprise buffer(s) and/or preservative(s) as appropriate, and suitable buffers and preservatives are disclosed in e.g. US Pharmacopoeia.

In still a further aspect of the invention there is provided an intradermal skin test composition, which comprises at least one antigen selected from the artificial pertussis toxin antigens reacting with antibodies induced by the native pertussis toxin, according to the invention, in an amount effective to produce an immunological skin reaction at a specific antibody titre in a subject, and a nontoxic pharmaceutically acceptable carrier and/or diluent. The skin test composition according to the invention may further comprise buffer(s) and/or preservative(s), as appropriate.

Useful carriers, diluents, buffers and preservatives are defined herein above.

SYNTHESIS OF THE PEPTIDE SEQUENCES ACCORDING TO THE INVENTION

Solid-phase (Merrifield) synthesis of the peptide sequences according to the invention has been performed in conventional manner, by coupling the amino acids to one another, whereby peptide bonds are formed, starting with a solid phase (resin) to which the C-terminal of the first amino acid is coupled, whereupon the C-terminal of the next amino acid is coupled to the N-terminal of the first amino acid, etc. Finally, the built-up peptide is released from the solid phase.

Specifically the following peptide sequences were synthesized:

A) H-Asp-Asp-Pro-Pro-Ala-Thr-Val-Tyr-Arg-Tyr-Asp-Ser-Arg-Pro-Pro-Glu-Asp-Lys-$NH_2$

B) H-Lys-Ser-Glu-Tyr-Leu-Ala-His-Arg-Arg-Ile-Pro-Pro-Glu-Asn-Ile-Arg-Arg-Thr-Arg-Val-OH

C) H-Lys-Ala-Phe-Val-Ser-Thr-Ser-Ser-Ser-Arg-Arg-Tyr-Thr-Glu-Val-Tyr-$NH_2$

D) H-Lys-Gly-Ile-Thr-Gly-Glu-Thr-Thr-Thr-Thr-Glu-Tyr-Ser-Asn-Ala-Arg-Tyr-Val-$NH_2$

E) H-Leu-Glu-His-Arg-Met-Gln-Glu-Ala-Val-Glu-Ala-Glu-Arg-Ala-Gly-Arg-Gly-Thr-Gly-His-Phe-Ile-Lys-$NH_2$

Synthesis of the peptide fragments was achieved using a Biosearch Sam Two (Biosearch, Inc. California USA) peptide synthesis machine using version 2.38 of Biosearch's peptide synthesis automation software for t-BOC amino acids. The standard (default) coupling constants were used for one gram of starting material (degree of substitution=0.33 meq/g).

The resin used for the synthesis of the peptide sequences A) and C) to E) (in amide form), was p-methylbenzhydrylamine resin and the resin used for the synthesis of B) was a standard Merrifield Resin. The suitably protected amino acids were:

| | |
|---|---|
| Boc-Ala-OH (Boc-L-Alanine) | Boc-Arg(Tos)-OH (a-Boc-N-Tosyl-L-Arginine) |
| Boc-Asn-OH (Boc-L-Asparagine) | Boc-Asp(OBzl)-OH (Boc-L-Aspartic Acid b-Benzyl Ester) |
| Boc-Glu(OBzl)-OH (Boc-L-Glutamic Acid gamma-Benzyl Ester) | Boc-Gln-OH (Boc-L-Glutamine) |
| Boc-Gly-OH (Boc-Glycine) | Boc-His(Tos)-OH (Boc-N-Tosyl-L-Histidine) |
| Boc-Ile-OH.½$H_2O$ (Boc-L-Isoleucine-½$H_2O$) | Boc-Leu-OH.$H_2O$ (Boc-L-Leucine-$H_2O$) |
| Boc-Lys(CL-Z)-OH Boc-e-o-Chloro-Benzyl-oxycarbonyl-L-Lysine) | Boc-Met-OH (Boc-L-Methionine) |
| Boc-Phe-OH (Boc-L-Phenylalanine) | Boc-Pro-OH (Boc-L-Proline) |
| Boc-Ser(Bzl)-OH (Boc-O-Benzyl-L-Serine) | Boc-Thr(Bzl)-OH (Boc-O-Benzyl-L-Threonine) |
| Boc-Tyr($Cl_2$-Bzl)-OH (Boc-O-2,6-Dichloro-benzyl-L-Tyrosine) | Boc-Val-OH (Boc-L-Valine) |

As to the details regarding amino acid concentration, solvent volumes, reaction times etc, the recommendations of the manufacturer (Biosearch) were followed.

Specifically the following chemicals listed below were use in the synthesis, cleavage and purification of the synthetic peptides.

| SUBSTANCE | GRADE | SUPPLIER |
|---|---|---|
| Acetyl imidazole | p.a. | Aldrich |
| Dimethyl formamide | p.a. | Fluka |
| Diisopropylethyl amine | Double-distilled from 1 g/l ninhydrin, then 5 g/l KOH. First 10% destillate discarded. | Aldrich |
| Hydroxybenzyl triazole | p.a. | Aldrich |
| Methylene chloride | HPLC | Fisons (UK) |
| Ninhydrin | p.a. | Aldrich |
| Potassium hydroxide | p.a. | |
| Diisopropyl carbodiimide | p.a. | Aldrich |
| Nitrogen | 4.1 (dry) | AGA |
| t-Boc amino acids | | Bachem |
| Hydrogen fluoride | | AGA |
| Resorcinol | | |
| Dimethyl sulfide | | |
| Hydroxybenzyl triazole | p.a. (synthesis) | Aldrich |
| Trifluoroacetic acid | sequanal (HPLC) | Aldrich |
| Acetonitrile | HPLC | Rathburn |
| Acetic acid | p.a. | Merck |

| SUBSTANCE | GRADE | SUPPLIER |
| --- | --- | --- |
| Diethyl ether | | Fluka |

The completed resin-bound peptides were removed from the synthesis chamber and rinsed with methanol, and dried to constant weight under vacuum.

CLEAVAGE OF THE PEPTIDES FROM THE RESIN SUPPORT

Portions (0.5 g) of the washed and dried resin-bound peptides were transferred to a cylindrical polytetrafluoroethylene (PTFE) chamber containing 1 g resorcinol, 6.5 ml dimethyl sulfide and a PTFE-coated magnet. The chamber was cooled to $-80°$ C. in a dry ice- ethanol bath. Hydrofluoric acid (HF) (final volume 10 ml) was then admitted to the chamber, which was then kept at $0°$ C. for 120 min on a magnetic stirrer. The acid was then removed using a water aspirator. The chamber was once again cooled to $-80°$ C. and 10 ml HF were admitted to the chamber, which was placed over a magnetic stirrer at $0°$ C. for 45 min. The acid was again removed using a water aspirator, and the remaining mixture transferred to a sintered glass filter. The resin/peptide mixture was then washed with 100 ml 10% (v/v) acetic acid and then with 50 ml diethyl eter. The acetic acid wash was also washed with 50 ml diethyl ether in a separatory funnel, and the ether phase removed from the aqueous phase. The pooled ether washes and the acetic acid wash were then evaporated and lyophilised, respectively, and the peptide product recovered. In all cases the peptide was recovered from the aqueous phase only.

The crude product was stored in glass vials in a dessicator at room temperature.

PURIFICATION OF THE SYNTHETIC PEPTIDES

The various components of the crude synthesis product were resolved by applying them to a reverse-phase C-18 silica high-pressure chromatorgraphy column using acetonitrile/$H_2O$ (0.1% v/v Trifluoroacetic acid (TFA)) as the mobile phase. 20 $\mu$g- 100 mg of the crude peptide were dissolved in up to 1 ml $H_2O$ (0.1% TFA), centrifuged and injected into a 1 ml loop on a Rheodyne (California, USA) HPLC injector. The solution was pumped through a custom-packed 10×500 mm Oligosil reverse-phase C-18 column (Skandinaviska Genetec, Sweden) using a 2152 gradient controller and two 2150 HPLC pumps (LKB, Sweden). The gradient was linear from 0-100% acetontrile in 60 min. The flow rate was 2 ml/min. The elution of the synthesis products was monitored at 206-238 nm using an LKB 2131 variable wavelength absorption monitor. Fractions were collected by hand and repurified if necessary by lyophilisation of the relevant fractions, redissolution and repeating of the chromatographic procedure. The final products were lyophilised and stored in glass vials at $-20°$ C.

PREPARATION OF PEPTIDE ANTIGENS FOR IMMUNOASSAY

Each of the above synthesized peptide sequences A) to E) was coupled to a carrier, i.e. bovine serum albumin (BSA) in the following manner to form av diagnostic antigen (coating antigen) which was used in ELISA.

One mg of peptide and 3.6 mg of BSA are dissolved in 2.0 ml of phosphate buffered saline (PBS), pH 7.4.

To this solution, 30 microliters of a 2.5% (w/v) aqueous glutardialdehyde solution is added.

The reaction mixture is incubated at room temperature ($20°-25°$ C.) for one hour, stopped by the addition of 0.5 ml of a 5M aqueous ethanolamine solution and then dialyzed against one liter of PBS at $+4°$ C. for four hours, with changes of the dialysing fluid after 30 minutes and after two hours.

Next the content of the dialysis bag is gelfiltrated through a column (2.5×60 cm) containing Sephacryl S-300 gel (Pharmacia, Uppsala, Sweden) equilibrated with PBS. Fractions of 3.0 ml are collected.

Fractions containing coupled material are pooled and the pooled material is used in ELISA as coating antigen and is added directly, without any previous dilution, to the microplate.

ENZYME-LINKED IMMUNOSORBENT ASSAYS (ELISA:s)

Bellow follows a general description of the ELISA:s. The antigen and the amount of antigen used for coating of the microplates (c.f. below), the conjugate and the dilution of the conjugate, the controls and the dilution of the controls and the time elapsed before the microplates are read may vary between the various assays. The differences are given after the general description.

GENERAL DESCRIPTION OF ELISA

Equipment

Microtitreplates (Dynatech, mod. nr 129B).
Antigen for coating of microplates (e.g. peptides and proteins).
Coatingbuffer: Phosphate buffered saline (PBS).
Incubation buffer: PBS+0.05% Tween 20 (v/v)
Aqueous washing fluid: 0.9% NaCl+0.05% Tween 20 Serum (e.g. human and animal reference and test sera) Conjugate (e.g. alkaline phosphatase conjugated swine anti-human IgG antibodies (Orion Diagnostica), goat anti-rabbit Ig antibodies (Sigma) and goat anti-mouse IgG antibodies (Sigma).
Enzyme substrate: p-nitrophenylphosphate tablets (Sigma), 1 mg/ml of substrate buffer (c.f. below)
Substrate buffer: 1M diethanolamine, pH 9.8, +0.5 mM $MgCl_2$+0.02% $NaN_3$.
Pipettes and testtubes

Performance

1. Coating of microplates. Microplates are incubated with 0.1 ml of antigen in PBS at room temperature ($20°-25°$ C.) over night.
2. Incubation with bovine serum albumin (BSA) and serum.
   The plates are washed four times and then incubated with 0.1 ml of 1% (w/v) BSA in PBS at $37°$ C. for one hour. After washing, 0.1 ml of serum appropriately diluted in incubation buffer, is added to the wells and the plate(s) is incubated at room temperature for one hour.
3. Incubation with conjugate. After washing, 0.1 ml of conjugate appropriately diluted in incubation buffer, is added to the wells and the plate(s) is incubated at room temperature for two hours.
4. After washing, 0.1 ml of the enzyme substrate solution is added to the wells. The plates are kept at room temperature and the absorbance at 405 nm is read after up to one hour.

SPECIFIC DESCRIPTIONS OF ELISA

Enzyme-Linked Immunosorbent Assays

Enzyme-linked immunosorbent assay (ELISA) for measuring the reaction between the synthetic peptides A) to E) and antibodies specifically induced by immunization with the native pertussis toxin (1), or antibodies after natural disease (2), respectively.

The peptides used as coating antigens in the ELISA were first treated as described under "Preparation of peptide antigens for immunoassay". Each assay was run in triplicate.

1. The positive serum sample was from a rabbit hyperimmunized with highly purified pertussis toxin (National Bacteriological Laboratory, Sweden), and the negative serum sample was from the same rabbit collected at the start of the immunization. Both sera were used at a 1/500 dilution. The conjugate used was an alkaline phosphatase goat anti-rabbit Ig conjugate (Sigma) diluted 1/500.

The plates were read after 15 minutes in an automated ELISA-reader (Titertek, Multiscan).

The results were as follows:

| Peptide | Rabbit Positive serum sample | Rabbit Negative serum sample |
|---|---|---|
|  | (absorbance) | (absorbance) |
| A) | 1.14 ± 0.07 | 0.12 ± 0.01 |
| B) | 1.34 ± 0.07 | 0.11 ± 0.01 |
| C) | 1.29 ± 0.12 | 0.026 ± 0.001 |
| D) | >1.5 | 0.013 ± 0.003 |
| E) | >1.5 | 0.018 ± 0.006 |

The significance level in Students' t-test was for each of the peptides A) to C) $p > 0.001$. For the peptides D) and E) it was not possible to calculate the significance level for the difference between positive and negative serum, but clearly the difference is even greater than for the peptides A) to C).

From the above results it is evident that the peptides A) to E) all bind strongly to antibodies induced by the native pertussis toxin.

2. The positive serum sample was a convalescent serum sample from a whooping cough patient, which was received from the National Bacteriological Laboratory (NBL) in Sweden. The human positive serum sample is so selected and adjusted that it in ELISA with the native toxin as antigen gives an absorbance at 405 nm of approx. 1.0 after one hour of incubation. The negative serum sample was a pool of sera from siblings, which was also received from NBL. Both sera were used at a 1/500 dilution. The conjugate used was an alkaline phosphatase swine anti-human IgG conjugate (Orion Diagnostica) diluted 1/100.

The plates were read after one hour in an automated ELISA-reader (Titertek, Multiscan).

The results from the assays were as follows:

| Peptide | Human Positive serum sample | Human Negative serum sample |
|---|---|---|
|  | (absorbance) | (absorbance) |
| A) | 0.86 ± 0.02 | 0.103 ± 0.008 |
| B) | 0.88 ± 0.08 | 0.120 ± 0.005 |
| C) | 0.17 ± 0.01 | 0.06 ± 0.01 |
| D) | 0.14 ± 0.04 | 0.05 ± 0.01 |
| E) | 0.23 ± 0.01 | 0.09 ± 0.02 |

The significance level in Students' t-test was for the peptides A), B), C) and E) $p < 0.001$ and for the peptide D) $0.01 < p < 0.02$.

As is evident from the above results all the peptides A) to E) according to the invention had a clearly higher absorbance with the positive serum samples than with the negative serum samples. Thus the tested peptides A) to E) function as antigens and bind to pertussis antibodies.

As a consequence it can be established that the peptides A) to E) specifically bind to antibodies induced by the native pertussis toxin in convalescent serum samples from whooping cough patients.

Enzyme-linked immunosorbent assay (ELISA) for measuring the reaction between synthetic peptides A) to E) and antibodies specifically induced by immunization of mice (1) or of siblings (2) with a whole cell vaccine, or of siblings (3) with a pertussis toxoid vaccine, respectively.

The peptides used as coating antigens in the ELISA were first treated as described under "Preparation of peptide antigens for immunoassay". Each assay was run in triplicate, the error of the readings within 10%.

1. Whole cell vaccine (Wellcome, England) hyperimmune serum samples and negative serum samples were obtained from five mice respectively. All sera were tested at a 1/500 dilution. The conjugate used was an alkaline phosphatase goat-anti mouse IgG conjugate (Sigma) diluted 1/500.

The plates were read after one hour in an automated ELISA reader (Titertec, Multiscan).

The results were as follows:

| Mouse | Sample | Peptide A | B | C | D | E |
|---|---|---|---|---|---|---|
| 1 | Control | 0.16 | 0.23 | 0.10 | 0.24 | 0.18 |
| 2 | Control | 0.10 | 0.10 | 0.10 | 0.12 | 0.08 |
| 3 | Control | 0.12 | 0.14 | 0.14 | 0.16 | 0.12 |
| 4 | Control | 0.12 | 0.13 | 0.12 | 0.13 | 0.10 |
| 5 | Control | 0.14 | 0.14 | 0.11 | 0.14 | 0.11 |
| 6 | Immunized | 0.21 | 0.29 | 0.27 | 0.29 | 0.26 |
| 7 | Immunized | 0.41 | 0.49 | 0.50 | 0.55 | 0.45 |
| 8 | Immunized | 0.75 | 0.80 | 0.71 | 0.84 | 0.74 |
| 9 | Immunized | 1.41 | 1.45 | 1.44 | 1.48 | 1.42 |
| 10 | Immunized | 1.14 | 1.47 | 1.41 | 1.59 | 1.42 |

From the above results it is evident that the peptides A) to E) all were able to specifically bind comparable amounts of antibodies in serum from mice immunized with whole cell vaccine (which contains pertussis toxin).

2. Pre- and postvaccination serum samples were collected from five siblings receiving a whole cell vacine (Wellcome, England). All sera were tested at a 1/500 dilution. The conjugate used was an alkaline phosphatase swine-anti human IgG conjugate (Orion Diagnostica) diluted 1/100.

The plates were read after one hour in an automated ELISA reader (Titertek, Multiscan).

The results were as follows:

| Sibling | Sample | Peptide | | | | |
|---|---|---|---|---|---|---|
| | | A | B | C | D | E |
| 1 | Pre | 0.05 | 0.07 | 0.06 | 0.07 | 0.07 |
| | Post | 0.07 | 0.26 | 0.21 | 0.22 | 0.20 |
| 2 | Pre | 0.12 | 0.07 | 0.05 | 0.07 | 0.07 |
| | Post | 0.41 | 0.30 | 0.20 | 0.26 | 0.21 |
| 3 | Pre | 0.21 | 0.49 | 0.52 | 0.49 | 0.46 |
| | Post | 0.06 | 0.31 | 0.31 | 0.31 | 0.28 |
| 4 | Pre | 0.10 | 0.18 | 0.14 | 0.19 | 0.15 |
| | Post | 0.23 | 0.72 | 0.73 | 0.67 | 0.62 |
| 5 | Pre | 0.06 | 0.16 | 0.12 | 0.15 | 0.13 |
| | Post | 0.06 | 0.12 | 0.08 | 0.10 | 0.10 |

As is evident from the above results all the peptides A) to E) were able to specifically bind antibodies in serum from siblings immunized with a whole cell vaccine (which contains pertussis toxin).

3. Pre- and postvaccination serum samples were collected from five siblings receiving a pertussis toxoid vaccine (Biken, Japan). All sera were tested at a 1/500 dilution. The conjugate used was an alkaline phosphates swine-anti human IgG conjugate (orion Diagnostica) diluted 1/100.

The plates were read after one hour in an automated ELISA reader (Titertek, Multiscan).
The results were as follows:

| Sibling | Sample | Peptide | | | | |
|---|---|---|---|---|---|---|
| | | A | B | C | D | E |
| 1 | Pre | 0.05 | 0.07 | 0.05 | 0.03 | 0.04 |
| | Post | 0.21 | 0.11 | 0.07 | 0.07 | 0.07 |
| 2 | Pre | 0.05 | 0.18 | 0.12 | 0.11 | 0.11 |
| | Post | 0.21 | 0.52 | 0.46 | 0.43 | 0.40 |
| 3 | Pre | 0.39 | 0.26 | 0.16 | 0.18 | 0.17 |
| | Post | 0.29 | 0.08 | 0.06 | 0.06 | 0.06 |
| 4 | Pre | 0.13 | 0.14 | 0.11 | 0.09 | 0.10 |
| | Post | 0.68 | 0.32 | 0.30 | 0.26 | 0.25 |
| 5 | Pre | 0.12 | 0.09 | 0.06 | 0.05 | 0.06 |
| | Post | 0.10 | 0.08 | 0.07 | 0.05 | 0.07 |

As is evident from the above results all the peptides A) to E) were able to specifically bind antibodies in serum from siblings immunized with a pertussis toxoid vaccine (which contains formalin inactivated pertussis toxin).

Enzyme-linked immunosorbent assay (ELISA) for measuring the reaction between native toxin and antibodies specifically induced by immunization of mice with the synthetic peptides A) to E).

The peptides used as antigens for immunization of mice were first treated as described under "Preparation of peptide antigens for immunoassay".

Groups of mice (NMRI) were immunized subcutaneously with three doses one month apart, 3×0, 5 ml, of respective peptide antigen using aluminium hydroxide as carrier. Serum samples were collected two months after the third dose. Microplates for ELISA were coated with purified pertussis toxin at a concentration of 1 μg/ml. Gelatin (1%) was used for blocking unspecific binding instead of BSA (c.f. "GENERAL DESCRIPTION OF ELISA"). The endpoint titre of the sera was determined by ten two-fold dilutions starting from a 1/20 dilution and using an absorbance value of 0.1 as cut off. The conjugate used was an goat-anti mouse IgG conjugate (Sigma) diluted 1/500.

The plates were read after 30 minutes in an automated ELISA reader (Titertek, Multiscan).
The results from the assay were as follows:

| Peptide | No | Responders | Mean Titre | Range |
|---|---|---|---|---|
| A | 11 | 9 | 6967 | 320–40960 |
| B | 17 | 3 | 640 | 320–2560 |
| C | 17 | 7 | 580 | 320–2560 |
| D | 12 | 1 | 2560 | — |
| E | 17 | 10 | 1194 | 320–10240 |
| Control | 12 | 0 | 67 | 20–160 |

It is evident from the above results that all the peptides A) to E) according to the invention are capable of inducing antibodies upon immunization, which have a clearly higher absorbance with the postvaccination samples than with the prevaccination samples. Thus the tested peptides A) to E) function as antigens and induce antibodies against pertussis toxin.

As a consequence it can be established that the toxin specifically binds to antibodies induced by the synthetic peptides A) to E) in postimmunization serum samples from mice.

I claim:
1. A polypeptide of the formula
 a) H-$X^1$-Asp-Asp-Pro-Pro-Ala-Thr-Val-Tyr-Arg-Tyr-Asp-Ser-Arg-Pro-Pro-Glu-Asp-$X^2$-Y,
 b) H-$X^1$-Ser-Glu-Tyr-Leu-Ala-His-Arg-Arg-Ile-Pro-Pro-Glu-Asn-Ile-Arg-Arg-Val-Thr-Arg-Val-$X^2$-Y,
 c) H-$X^1$-Ala-Phe-Val-Ser-Thr-Ser-Ser-Ser-Arg-Arg-Tyr-Thr-Glu-Val-Tyr-$X^2$-Y,
 d) H-$X^1$-Gly-Ile-Thr-Gly-Glu-Thr-Thr-Thr-Thr-Glu-Tyr-Ser-Asn-Ala-Arg-Tyr-Val-$X^2$-Y, or
 e) H-$X^1$-Leu-Glu-His-Arg-Met-Gln-Glu-Ala-Val-Glu-Ala-Glu-Arg-Ala-Gly-Arg-Gly-Thr-Gly-His-Phe-Ile-$X^2$-Y
in which $X^1$ and $X^2$ each represents an optional coupling-facilitating amino acid residue, and Y represents —OH or —$NH_2$.

2. An artificial pertussis toxin antigen; said antigen being a polypeptide which is optionally coupled to carrier; said polypeptide being selected from the group consisting of:
a) the polypeptide H-$X^1$-Asp-Asp-Pro-Pro-Ala-Thr-Val-Tyr-Arg-Tyr-Asp-Ser-Arg-Pro-Pro-Glu-Asp-$X^2$-Y b) the polypeptide H-$X^1$-Ser-Glu-Tyr-Leu-Ala-His-Arg-Arg-Ile-Pro-Pro-Glu-Asn-Ile-Arg-Arg-Val-Thr-Arg-Val-$X^2$-Y c) the polypeptide H-$X^1$-Ala-Phe-Val-Ser-Thr-Ser-Ser-Ser-Arg-Arg-Tyr-Thr-Glu-Val-Tyr-$X^2$-Y d) the polypeptide H-$X^1$-Gly-Ile-Thr-Gly-Glu-Thr-Thr-Thr-Thr-Glu-Tyr-Ser-Asn-Ala-Arg-Tyr-Val-$X^2$-Y e) the polypeptide H-$X^1$-Leu-Glu-His-Arg-Met-Gln-Glu-Ala-Val-Glu-Ala-Glu-Arg-Ala-Gly-Arg-Gly-Thr-Gly-His-Phe-Ile-$X^2$-Y and parts thereof capable of reacting with antibodies induced by the native pertussis toxin;

wherein $X^1$ and $X^2$ each represent an optional coupling-facilitating amino acid residue for coupling said polypeptide to said carrier; and Y represents —OH or —NH$_2$.

3. A vaccine composition which comprises a pharmaceutically-acceptable carrier or diluent in combination with an artificial pertussis toxin antigen capable of eliciting a protective response against whooping cough; said antigen being a polypeptide which is optionally coupled to carrier; said polypeptide being selected from the group consisting:

a) the polypeptide

H-X$^1$-Asp-Asp-Pro-Pro-Ala-Thr-Val-Tyr-Arg-Tyr-Asp-Ser-Arg-Pro-Pro-Glu-Asp-X$^2$-Y b) the polypeptide H-X$^1$-Ser-Glu-Tyr-Leu-Ala-His-Arg-Arg-Ile-Pro-Pro-Glu-Asn-Ile-Arg-Arg-Val-Thr-Arg-Val-X$^2$-Y c) the polypeptide H-X$^1$-Ala-Phe-Val-Ser-Thr-Ser-Ser-Ser-Arg-Arg-Tyr-Thr-Glu-Val-Tyr-X$^2$-Y d) the polypeptide H-X$^1$-Gly-Ile-Thr-Gly-Glu-Thr-Thr-Thr-Thr-Glu-Tyr-Ser-Asn-Ala-Arg-Tyr-Val-X$^2$-Y e) the polypeptide H-X$^1$-Leu-Glu-His-Arg-Met-Gln-Glu-Ala-Val-Glu-Ala-Glu-Arg-Ala-Gly-Arg-Gly-Thr-Gly-His-Phe-Ile-X$^2$-Y and parts thereof capable of eliciting a protective response against whooping cough;

wherein $X^1$ and $X^2$ each represent an optional coupling-facilitating amino acid residue for coupling said polypeptide to said carrier; and Y represents —OH or —NH$_2$.

4. A vaccine composition according to claim 3, wherein said pertussis toxin antigen(s) is (are) present in an amount effective to protect a subject from the disease whooping cough.

5. A vaccine composition according to claim 3, which further consists of an antigen adjuvant in an amount which together with an amount of said pertussis toxin antigen(s) is effective to protect a subject from the disease whooping cough.

6. A vaccine composition according to claim 3, which further consists of buffer(s) and/or preservative(s).

* * * * *